(12) United States Patent
Hudson

(10) Patent No.: US 9,119,456 B1
(45) Date of Patent: Sep. 1, 2015

(54) LOTION APPLICATOR WITH ADJUSTABLE HANDLE

(71) Applicant: William Russell Hudson, Fort Worth, TX (US)

(72) Inventor: William Russell Hudson, Fort Worth, TX (US)

( * ) Notice: Subject to any disclaimer, the term of this patent is extended or adjusted under 35 U.S.C. 154(b) by 0 days.

(21) Appl. No.: 14/174,578

(22) Filed: Feb. 6, 2014

Related U.S. Application Data

(60) Provisional application No. 61/763,114, filed on Feb. 11, 2013.

(51) Int. Cl.
*A45D 34/04* (2006.01)
*A61M 35/00* (2006.01)
*A45D 40/26* (2006.01)

(52) U.S. Cl.
CPC ............... *A45D 34/04* (2013.01); *A45D 40/26* (2013.01); *A45D 2200/1081* (2013.01); *A61M 35/003* (2013.01)

(58) Field of Classification Search
CPC .. A61M 33/003; A61M 33/006; A61H 7/003; A61H 7/005; A47K 7/022; A47K 7/028; A45D 2200/1081; A45D 40/26; A45D 40/28; A45D 40/262; A45D 34/04; A45D 34/042; A45D 33/34; A45D 33/36
USPC ........... 15/144.1–144.4, 104.001, 160, 209.1, 15/210.1, 244.1, 244.2; 132/320; 401/6; 601/135, 137, 138; 604/1; D28/7, 63; D24/119, 214
See application file for complete search history.

(56) References Cited

U.S. PATENT DOCUMENTS

| | | | | |
|---|---|---|---|---|
| 4,396,028 A | * | 8/1983 | Waggoner | 15/144.4 |
| D343,680 S | * | 1/1994 | Salerno | D24/119 |
| 5,566,418 A | * | 10/1996 | Steffen et al. | 15/244.1 |
| 5,568,669 A | * | 10/1996 | Godown | 15/143.1 |
| 5,842,488 A | * | 12/1998 | Belleau et al. | 132/320 |
| 6,026,535 A | * | 2/2000 | Lankowski | 15/209.1 |
| 6,415,470 B1 | * | 7/2002 | Ramrattan | 15/144.4 |
| 7,185,385 B2 | * | 3/2007 | Kohler | 15/104.001 |
| 8,646,142 B2 | * | 2/2014 | Ferrara et al. | 15/104.001 |
| 2002/0092107 A1 | * | 7/2002 | Kimbro | 15/143.1 |
| 2008/0052856 A1 | * | 3/2008 | Lin | 15/172 |
| 2008/0307595 A1 | * | 12/2008 | Zielinski | 15/144.4 |
| 2012/0167322 A1 | * | 7/2012 | Jaworski et al. | 15/144.1 |

FOREIGN PATENT DOCUMENTS

JP 2000-175834 * 6/2000

* cited by examiner

*Primary Examiner* — Mark Spisich
(74) *Attorney, Agent, or Firm* — Kenneth L Tolar

(57) ABSTRACT

A lotion applicator includes an elongated, telescoping shaft having an applicator head attached to an end thereof. Pivotally connected to an opposing end of the shaft is an angularly adjustable handle. Accordingly, a user places lotion on the applicator head and reciprocates it on a desired portion of the body. If necessary to reach a certain area, the shaft can be extended or retracted, and the handle can be adjusted to a desired angle.

5 Claims, 2 Drawing Sheets

LOTION APPLICATOR WITH ADJUSTABLE HANDLE

CROSS REFERENCE TO RELATED APPLICATIONS

This application is entitled to the benefit of provisional patent application No. 61/763,114, filed on Feb. 11, 2013, the specification of which is incorporated herein by reference.

BACKGROUND OF THE INVENTION

The present invention relates to a tool for easily applying lotion to a desired body part.

DESCRIPTION OF THE PRIOR ART

Applying lotions to certain areas of the body can be difficult and challenging. Typically, the lotion is first delivered to the hands, which are then used to spread the lotion over other desired body parts. However, the elderly or those who are otherwise inflexible are unable to reach certain areas of the back or other remote areas without assistance. Conventional lotion applicators that purportedly overcome the aforementioned problems typically include an elongated handle having a sponge or brush at a distal end. However, because neither the handle nor the brush is adjustable, a user is often unable to effectively access certain remote areas.

Accordingly, there is currently a need for an improved lotion applicator that overcomes the above-described problems. The present invention addresses this need by providing a lotion applicator having a telescoping shaft and an angularly adjustable handle for easily positioning an applicator head, as desired.

SUMMARY OF THE INVENTION

The present invention relates to a lotion applicator comprising an elongated, telescoping shaft having an applicator head attached to an end thereof. Pivotally connected to an opposing end of the shaft is an angularly adjustable handle. Accordingly, a user places lotion on the applicator head and reciprocates it on a desired portion of the body. If necessary to reach a certain area, the shaft can be extended or retracted, and/or the handle can be adjusted to a desired angle.

It is therefore an object of the present invention to provide a lotion applicator that allows a user to more easily access all areas of the body.

It is another object of the present invention to provide a lotion applicator having an adjustable handle for more easily reaching otherwise inaccessible areas.

Other objects, features and advantages of the present invention are readily apparent from the following detailed description of the preferred embodiment, the attached drawings and the appended claims.

DESCRIPTION OF THE PREFERRED EMBODIMENT

Figure 1:
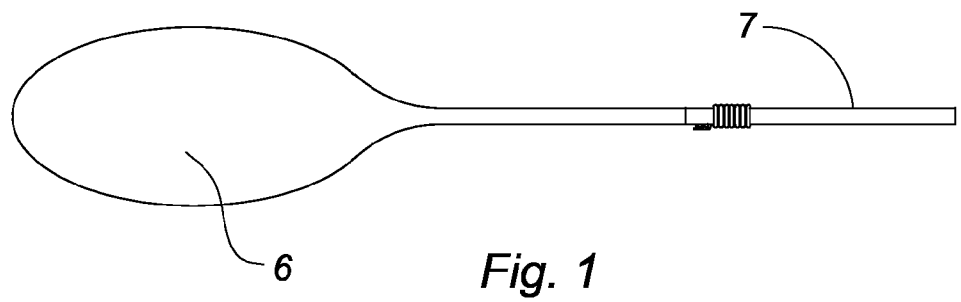
FIG. 1 is a top, plan view of the lotion applicator according to the present invention.
Figure 2:
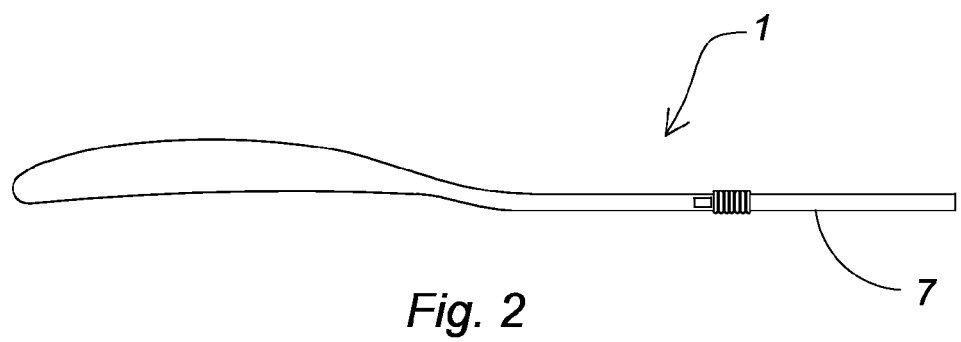
FIG. 2 is a side view of the applicator.
Figure 3:
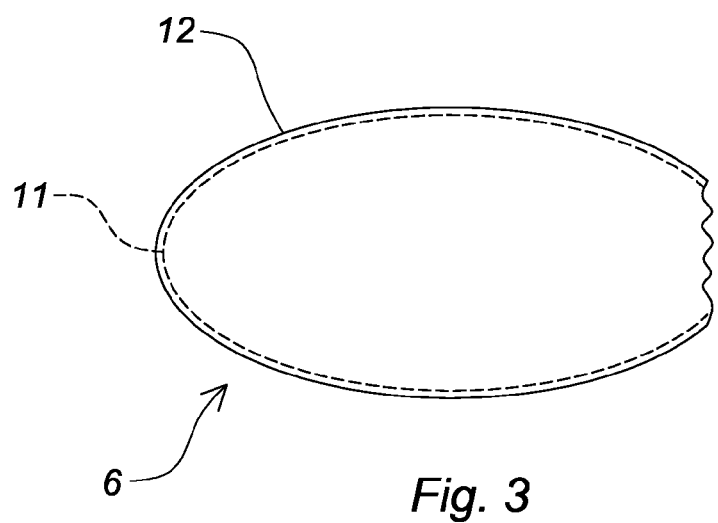
FIG. 3 an isolated, top view of the applicator head.
Figure 4:
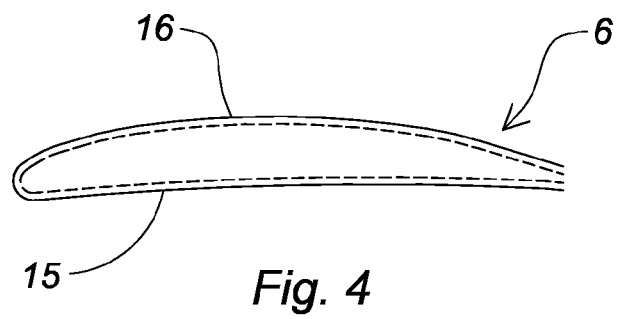
FIG. 4 an isolated, side view of the applicator head.
Figure 5:
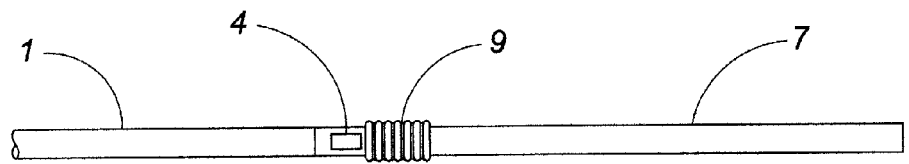
FIG. 5 is an isolated view of the shaft.
Figure 6:
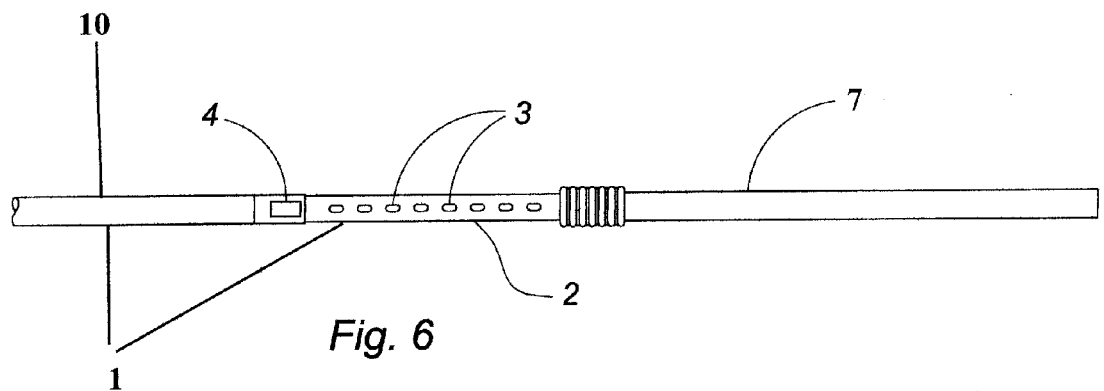
FIG. 6 is an isolated view of the shaft in an extended position.
Figure 7:
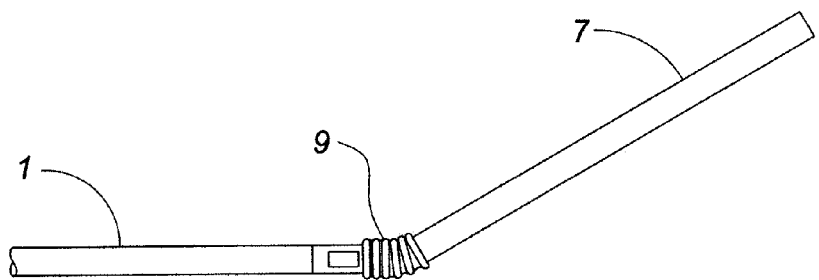
FIG. 7 is an isolated view of the shaft with the handle obliquely positioned relative thereto.
Figure 8:
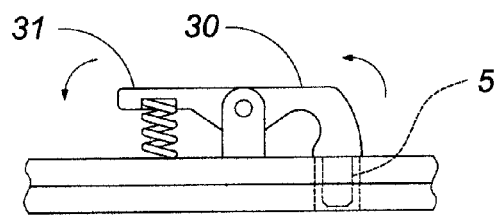
FIG. 8 is an isolated view of the spring-biased latch.
Figure 9:
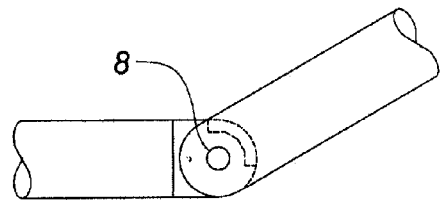
FIG. 9 is an isolated view of the ball-detent mechanism.

The present invention relates to a lotion applicator comprising an elongated shaft 1 formed of at least two length-adjustable sections. An inner section 2 having a plurality of longitudinal openings 3 is telescopically received within an outer section 10 having a spring-biased latch 4 at an end thereof. The latch includes a pivotal lever 30 with a pin 5 at a first end and a spring-biased button 31 at an opposing end. Depressing the button 31 lifts the pin 5 from a receiving aperture, allowing a user to adjust the length of the shaft, as desired.

Attached to the distal end of the outer section is an ovate applicator head 6 formed of a rigid inner shell 11 encapsulated by an outer layer 12 of silicone rubber. The head includes a relatively planar lower surface 15 and an arcuate upper surface 16, either of which can be used to apply lotion according to the contour of the target area. A handle 7 is pivotally connected to the distal end of the inner section with a spring-biased, ball-detent mechanism 8 that allows the handle to be locked in either of a 0, 30, 60 or 90-degree angle relative to the shaft. An accordion-style, rubber hinge-guard 9 covers the ball-detent mechanism.

Accordingly, a user places lotion on either surface of the applicator head and reciprocates it on a desired portion of the body. If necessary to reach a certain area, the shaft can be extended or retracted, and the handle can be adjusted to a desired angle.

The above-described device is not limited to the exact details of construction and enumeration of parts provided herein. Furthermore, the size, shape and materials of construction of the various components can be varied.

Although there has been shown and described the preferred embodiment of the present invention, it will be readily apparent to those skilled in the art that modifications may be made thereto which do not exceed the scope of the appended claims. Therefore, the scope of the invention is only to be limited by the following claims.

What is claimed is:
1. A lotion applicator with adjustable handle comprising:
an elongated shaft formed of at least two length-adjustable sections, said shaft having a first end and a second end;
an ovate applicator head at the first end of said shaft, said head having a substantially planar lower surface and an arcuate, convex upper surface allowing a user to apply lotion with either of said lower surface and said upper surface according to a contour of a target area;
a handle pivotally connected to the second end of said shaft that allows a user to selectively position said applicator head relative a body part.
2. The lotion applicator according to claim 1 wherein said shaft is formed of an inner section having a plurality of longitudinal openings thereon, and an outer section telescopically receiving said inner section, said outer section having a spring-biased latch at an end thereof that removably seats within any one of said openings to fix said shaft at a desired length.
3. The lotion applicator according to claim 2 wherein said applicator head is formed of a rigid inner shell encapsulated by an outer layer of rubber.

4. The lotion applicator according to claim 3 wherein said handle is pivotally connected to the distal end of the inner section with a spring-biased, ball-detent mechanism that allows the handle to be locked in either of a 0, 30, 60 or 90-degree angle relative to the shaft.

5. The lotion applicator according to claim 4 further comprising an accordion-style, rubber hinge-guard encapsulating said ball-detent mechanism.

\* \* \* \* \*